US007001615B1

(12) United States Patent
Singh et al.

(10) Patent No.: US 7,001,615 B1
(45) Date of Patent: Feb. 21, 2006

(54) SUSTAINED RELEASE OPHTHALMIC, OTIC AND NASAL SUSPENSION

(75) Inventors: Onkar N. Singh, Arlington, TX (US); Ernesto J. Castillo, Arlington, TX (US)

(73) Assignee: Alcon, Inc., Hunenberg (CH)

( * ) Notice: Subject to any disclaimer, the term of this patent is extended or adjusted under 35 U.S.C. 154(b) by 672 days.

(21) Appl. No.: 10/295,284

(22) Filed: Nov. 15, 2002

Related U.S. Application Data

(60) Provisional application No. 60/340,199, filed on Dec. 7, 2001.

(51) Int. Cl.
*A61K 9/14* (2006.01)

(52) U.S. Cl. .................... 424/488; 424/486
(58) Field of Classification Search ............... 424/488, 424/486
See application file for complete search history.

(56) References Cited

U.S. PATENT DOCUMENTS

| | | | |
|---|---|---|---|
| 2,774,789 A | 12/1956 | Tullar | 260/570.6 |
| 3,202,660 A | 8/1965 | Zeile et al. | 260/254 |
| 3,309,406 A | 3/1967 | Kunz et al. | 260/570.7 |
| 3,619,370 A | 11/1971 | Weinstock | 260/247.1 |
| 3,655,663 A | 4/1972 | Wasson | 260/247.1 |
| 3,657,237 A | 4/1972 | Weinstock | 260/247.1 |
| 3,663,607 A | 5/1972 | Barrett | 260/501.1 |
| 3,836,671 A | 9/1974 | Barrett et al. | 424/324 |
| 3,857,952 A | 12/1974 | Wooldridge et al. | 424/324 |
| 3,867,519 A | 2/1975 | Michaels | 424/19 |
| 3,962,414 A | 6/1976 | Michaels | 424/19 |
| 3,987,163 A | 10/1976 | Rankin | 424/78 |
| 4,012,444 A | 3/1977 | Lunts et al. | 260/559 |
| 4,127,674 A | 11/1978 | Leopold | 424/324 |
| 4,207,890 A | 6/1980 | Mamajek et al. | 128/223 |
| 4,252,984 A | 2/1981 | Manoury et al. | 564/349 |
| 4,271,143 A | 6/1981 | Schoenwald et al. | 424/78 |
| 4,407,792 A | 10/1983 | Schoenwald et al. | 424/81 |
| 4,462,982 A | 7/1984 | Samejima et al. | 424/35 |
| 4,521,414 A | 6/1985 | Chiou et al. | 514/229 |
| 4,694,022 A | 9/1987 | Gerson et al. | 514/554 |
| 4,859,462 A | 8/1989 | Chow et al. | 424/79 |
| 4,911,920 A | 3/1990 | Jani et al. | 424/78 |
| 4,983,392 A | 1/1991 | Robinson | 424/427 |
| 5,188,826 A | 2/1993 | Chandrasekaran et al. | 424/78.04 |
| 5,192,535 A | 3/1993 | Davis et al. | 424/78.04 |
| 5,212,162 A | 5/1993 | Missel et al. | 514/54 |
| 5,461,081 A | 10/1995 | Ali et al. | 514/772.3 |
| 5,540,930 A | 7/1996 | Guy et al. | 424/427 |
| 5,635,172 A | 6/1997 | Jani et al. | 424/78.04 |
| 5,747,061 A | 5/1998 | Amselem et al. | 424/427 |
| 5,958,443 A | 9/1999 | Viegas et al. | 424/427 |

FOREIGN PATENT DOCUMENTS

| | | |
|---|---|---|
| EP | 0 429 732 A * | 6/1991 |
| EP | 0 429 732 A1 | 6/1991 |
| GB | 2 130 585 A | 6/1984 |
| WO | WO 89/06964 | 8/1989 |
| WO | WO 92/11871 | 7/1992 |

OTHER PUBLICATIONS

Baldwin et al., "$\beta_1$-Selective Adrenoceptor Antagonists: Examples of the 2-[4-[3-(Substituted-amino)-2-hydroxypropoxy]phenyl]limidazole Class," *J. Med. Chem.*, vol. 26, pp. 950-957 (1983).

Erhardt et al., "Ultra-Short Acting $\beta$-Adrenergic Receptor Blocking Agents. 3. Ethylenediamine Derivatives of (Aryloxy)propanolamines Having Esters on the Aryl Function," *J. Med Chem.*, vol. 26, pp. 1109-1112 (1983).

Evans et al., "$\beta$-Adrenergic Receptor Blockers as Therapeutic Agents," *J. Med. Chem.*, vol. 14, pp. 81-90 (1979).

Gennaro, A. *Remington's Pharmaceutical Science*, Mack Publishing Company, Easton, PA (1985) "How to Use Ophthalmic Ointment".

Heath et al., Adsorption of $\beta$-Adrenoceptor Antagonists to Amberlite® Resin, *Br. J. Clin. Pharmac.*, vol. 15, pp. 490-492 (1983).

Heyd, "Polymer-Drug Interaction: Stability of Aqueous Gels Containing Neomycin Sulfate," *J. of Pharm. Sciences*, vol. 60 (9), pp. 1343-1345 (1971).

Kierstead et al., "$\beta_1$-Selective Adrenoceptor Antagonists. 1. Synthesis and $\beta$-Adrenergic Blocking Activity of a Series of Binary (Aryloxy)propanolamines," *J. Med. Chem.*, vol. 26, pp. 1561-1569 (1983).

Large et al., "$\beta$-Adrenergic Blocking Agents," *J. Med. Chem.*, vol. 26, pp. 352-357 (1983).

Machin et al., "$\beta_1$-Selective Adrenoceptor Antagonists. 3. 4-Azolyl-Linked Phenoxypropanolamines," *J. Med. Chem.*, vol. 27, pp. 503-509 (1984).

McClure et al., "Antihypertensive $\beta$-Adrenergic Blocking Agents: N-Arlkyl analogues of 2-[3-(tert-Butylamino)-2-hydroxypropoxy]-3-cyanopyride[1] , " *J. Med. Chem.*, vol. 26., pp. 649-657 (1983).

Pitha et al., "$\beta$-Adrenergic Antagonists with Multiple Pharmacophores: Persistent Blockade of Receptors," *J. Med. Chem.*, vol. 26, pp. 7-11 (1983).

Rohm and Hass Product Brochure for Amberlite® and Duolite® (1991).

Schoenwald et al., "Influence of High-Viscosity Vehicles on Miotic Effect of Pilocarpine," *J. of Pharm. Sciences*, vol. 67(9), pp. 1280-1283 (1978).

(Continued)

*Primary Examiner*—Carlos A. Azpuru
(74) *Attorney, Agent, or Firm*—Patrick M. Ryan

(57) ABSTRACT

Sustained release suspension formulations for ophthalmic, otic and nasal administration are disclosed. The formulations comprise a basic active, a cation exchange resin, and a combination of a polymeric suspending agents to provide superior resuspendability.

9 Claims, No Drawings

OTHER PUBLICATIONS

Stalker "Enhancement of Ocular Drug Bioavailability Through the Use of Micronized, Functionalized Polymers as Carriers of Therapeutic Agents," Dissertation submitted at the University of Kentucky (1983).

Stalker et al., "Enhancement of Ocular Drug Bioavailablity Through the Use of Drug-Resin Complexes I: Tear Film Concentrations Versus Time Profiles for Pencillin-G" Abstract of Papers Presented Before the American Pharmaceutical Association Academy of Pharmaceutical Sciences 33rd National Meeting, San Diego, CA; vol. 12 (2), p. 116, No. 57 (1982).

Stalker et al., "Enhancement of Ocular Drug Bioavailability Through the Use of Drug-Resin Complexes II: Aqueous Humor Concentrations Versus Time Profiles for Nafcillin," Abstract of Papers Presented Before the American Pharmaceutical Association Academy of Pharmaceutical Sciences 33rd National Meeting, San Diego, CA; vol. 12 (2), p. 116, No. 58 (1982).

Stevens et al., "Drug Release Profiles of Ophthalmic Formulations. 1. Instrumentations," *Anal. Chem.*, vol. 64, pp. 715-723 (1992).

* cited by examiner

SUSTAINED RELEASE OPHTHALMIC, OTIC AND NASAL SUSPENSION

This application claims priority to U.S. Provisional Application Ser. No. 60/340,199, filed Dec. 7, 2001.

BACKGROUND OF THE INVENTION

This invention relates to ophthalmic, otic and nasal suspension formulations containing water-insoluble resins as drug delivery aids. In particular, this invention relates to the use of combinations of polymeric suspending agents to improve the physical stability of suspension formulations containing water-insoluble drug delivery aids.

U.S. Pat. No. 4,911,920, the entire contents of which are incorporated by reference, discloses sustained release formulations for glaucoma therapy, wherein the formulations comprise a basic active and a cationic exchange resin dispersed in an aqueous solution or gel of a polyanionic polymer. The cationic-exchange resin in the '920 formulations can be "any pharmaceutical grade cationic exchange resin" (Col. 3, lines 65–66 of the '920 patent) and include the "Amberlite" (Rohm & Haas) and "Dowex" (Dow Chemical Co.) lines of commercially available resins. The polyanionic polymers have a molecular weight of from about 50,000 to about 6 million, and are characterized as having carboxylic acid functional groups. Preferred polyanionic polymers are the carboxy vinyl polymers known as carbomers, such as those available under the trade name Carbopol from the B.F. Goodrich Company. Carbopol 934 and Carbopol 940 are specifically preferred.

U.S. Pat. No. 5,188,826 discloses an ophthalmic gel suspension for treating dry eye. The suspension formulations remain as a gel in the eye for a prolonged time, and release water and one or more ophthalmic demulcents or vasoconstrictors. The suspension formulations contain a water-insoluble, lightly cross-linked, carboxyl-containing polymer having a particle size of not more than 50 $\mu$m in equivalent spherical diameter. The demulcent is preferably at least one of sodium carboxymethyl cellulose, hydroxyethyl cellulose, hydroxypropylmethyl cellulose, methyl cellulose, dextran 70, gelatin, glycerin, polyethylene glycol, polysorbate 80, propylene glycol, polyvinyl alcohol or polyvinylpyrrolidone. Particularly preferred as the carboxyl-containing polymer is Carbopol 976. The suspension formulations do not contain a prescription drug.

U.S. Pat. No. 5,192,535 discloses suspension formulations of ophthalmic drugs that have suitably low viscosities to permit easy administration in drop form, but which rapidly gel in the eye to provide sustained drug release. The suspension formulations are formulated at a pH of from about 3 to about 6.5 and contain a water-insoluble, carboxyl-containing polymer prepared by polymerizing one or more carboxyl-containing monethylenically unsaturated monomers and less than about 5% by weight of a cross-linking agent. Carbopol 976 and polycarbophil are identified as examples of suitable carboxyl-containing polymers. Ion exchange resins may be included as one type of adjuvant in the suspension formulations. Demulcents are identified as one of many types of medicaments suitable for use in the suspension formulations.

WO 92/11871 discloses suspension formulations for controlled delivery of pharmaceutical compounds. The sustained release compositions are generally formed as follows. First, one or more pharmaceutical compounds are reversibly loaded onto ion exchange resin particles. Second, the loaded ion exchange resin particles are incorporated into an erodible polymeric complex. The polymeric matrix coating incorporating the loaded ion exchange resin particle at least partially encloses the loaded exchange resin particle as either a solid matrix or enclosing microcapsule. Preferably, the polymeric matrix will totally enclose at least one or more of the drug-loaded ion exchange resin particles. In this manner, the loaded pharmaceutical compound is locked into the ion exchange resin particle and shielded from external solvent effects, enhancing chemical stability and storage stability, for example. The polymer matrix may be formed from any phsiologically compatible erodible polymer. The polymers should be substantially non-ionic. Preferred exemplary polymers include polyvinylpyrrolidone, poly(methylvinylether/maleic anhydride) and mixtures thereof. Incorporation of the loaded ion exchange resin particles into the polymeric matrix may be accomplished through a variety of methods, including precipitation and phase coacervation techniques.

SUMMARY OF THE INVENTION

The aqueous, liquid suspension formulations of the present invention contain an ion exchange resin to provide sustained release properties and a polymeric suspending component to provide improved settling and resuspendability properties. The polymeric suspending component consists essentially of a combination of a carboxyvinyl polymer and a polymer selected from the group consisting of hydroxyethyl cellulose; hydroxypropyl cellulose; and carboxymethyl cellulose. The formulations also contain one or more ophthalmic, otic or nasal drugs.

Among other factors, the present invention is based on the finding that suspension formulations containing select combinations of polymeric suspending agents had unexpectedly superior resuspendability rates compared to similar formulations containing single polymers or other combinations of polymers.

DETAILED DESCRIPTION OF THE INVENTION

Unless indicated otherwise, all ingredient concentrations are listed as % (w/v).

The formulations of the present invention comprise a basic active, a cation exchange resin, and a combination of polymeric suspending agents. The formulations of the present invention are aqueous, liquid compositions.

Basic Active

As used herein, "basic active" means a positively-charged, ophthalmically, otically or nasally acceptable active agent. Suitable basic actives include beta blockers, such as betaxolol, timolol, befunolol, labetalol, propanolol, bupranolol, metaprolol, bunalol, esmalol, pindolol, carteolol, hepunolol, metipranolol, celiprolol, azotimolol, diacetolol, acebutolol, salbutamol, atenulol, isoxaprolol, and the like. Basic actives also include the following: pilocarpine, epinephrine; proepinephrine, norepinephrine; pronorepinephrine, clonidine and clonidine derivatives, brimonidine and prostaglandins. Other examples include steroidal and nonsteroidal antiinflammatory agents such as dexamethasone, hydrocortisone, prednisolone, rimexolone and diclofenac, anti-infective agents such as ciprofloxacin, moxifloxacin and trovafloxacin, and anti-allergy agents such as olopatadine and emedastine.

Thus, the basic active component of the present invention is defined as an ophthalmically, otically or nasally acceptable pharmaceutically active compound having a cationic nature in an aqueous medium in the pH range of from 3.0 to 8.5. The most preferred basic actives are betaxolol, timolol and dipivefrin. The compositions of the present invention may contain two or more basic active components in combination. The basic active component is present at a level of about 0.01 to 4.0%, preferably from 0.10 to 1.0%.

Cation Exchange Resin

The cation exchange resin component of the formulations of the present invention provides a means of sustained release of the basic active. Such resins are characterized as either strongly acidic, such as those having sulfonic acid functionality, or weakly acidic, such as those having carboxylic acid functionality, cation exchangers. The average particle size of the commercially available forms of the resins is about 40 to 150 microns. The particle size of the resin is critical for topically administrable ophthalmic compositions. Accordingly, for topically administrable ophthalmic compositions, commercially available resin particles are reduced by known techniques, including grinding, ball milling and microfluidization, to a particle size of about 20 $\mu$m or less, such that the average particle size is $\leq$10 $\mu$m. Preferably, the resin particles are reduced to a particle size of about 10 $\mu$m or less. Ion exchange resins are typically used in an amount from about 0.05 to about 10%. Preferably, the ion exchange resin is used in a 0.5:1–1.5:1 ratio with the basic active (resin:drug). Most preferably, the ion exchange resin is used in a 1:1 ratio with the basic active.

Any pharmaceutical grade cationic ion exchange resin is suitable for the suspension formulations of the present invention. Such resins are available, for example, under the "Amberlite" trade name from Rohm & Haas and under the "Dowex" trade name from Dow Chemical Co. Suitable resins include, for example, Amberlite IRP-69, Amberlite IR-118H and Amberlyst 131 (4% cross-linking).

Polymeric Suspending Component

The polymeric suspending component contained in the compositions of the present invention consists essentially of a combination of a carboxyvinyl polymer and a polymer selected from the group consisting of hydroxyethyl cellulose; hydroxypropyl cellulose; and carboxymethyl cellulose.

Carboxyvinyl Polymer

The carboxyvinyl polymers useful in the present invention are ophthalmically, otically or nasally acceptable and have an approximate molecular weight of from about 50,000 to about 6 million. The polymers are characterized as having carboxylic acid functional groups and preferably contain from 2 to 7 carbon atoms per functional group. Preferred carboxyvinyl polymers include water-soluble and water-swellable carbomers, available under the trade name CARBOPOL from the B.F. Goodrich Company, and maleic anhydride polymers, such as those available under the trade name EMA from the Monsanto Company. The commercially available polymers Carbopol 934P, 940 and 974P are most preferred. The amount of carboxyvinyl polymer present in the suspension formulations of the present invention ranges from about 0.05 to 1.0%, and preferably 0.10 to 0.3%.

Cellulose Polymer

In addition to a carboxyvinyl polymer, the polymeric suspending component contains a cellulose polymer selected from the group consisting of hydroxyethyl cellulose (HEC); hydroxypropylmethyl cellulose (HPMC), and carboxymethyl cellulose (CMC). HEC and HPMC are commercially available. CMC is commercially available in the form of a sodium salt (Na-CMC) or calcium salt (Ca-CMC).

The amount of cellulose polymer present in the suspension formulations of the present invention ranges from about 0.05 to 1%, and preferably 0.1 to 0.5%. The molecular weight range for the cellulose polymer will generally be from 10,000 to 1.5 million.

Other Components

The suspension compositions of the present invention optionally include other components, such as pharmaceutically acceptable buffers; tonicity agents; comfort-enhancing agents; solubilizing aids; pH-adjusting agents; antioxidants; preservatives and stabilizing agents. Suitable preservatives include: benzalkonium chloride, thimerosal, chlorobutanol, methyl paraben, propyl paraben, phenyl-ethyl alcohol, sorbic acid, polyquaternium-1 and other agents known to those skilled in the art. Preservative adjuncts such as edetate disodium and boric acid are also suitable. Typically such preservatives are employed at a level of from 0.001 to 1.0% by weight. The tonicity, or osmolality, of the product can be adjusted to hypotonicity, isotonicity or hypertonicity relative to normal tears by use of conventional materials known to the art. Such tonicity agents, however are limited to nonionic compounds and typically, when employed, range from 0.01 to 10% in the final product. Nonionic agents include mannitol, sorbitol, dextrose, glycerine, propyleneglycol and polyethyleneglycol.

Representative compounding procedures for the suspension formulations of the present invention include the following.

1. The cationic exchange resin component is dispersed in 10 to 50 vol. percent of total water taken in formulation, and then basic active is dispersed and/or dissolved with stirring. The carboxyvinyl polymer and cellulose polymers are added as aqueous dispersions. The pH of the product can be adjusted to the desired value by varying basic active/carboxyvinyl polymer/resin ratio. If desired, final pH of product can be adjusted with addition of either NaOH or HCl or other pH-adjusting agent. The preferred pH range for ophthalmic formulations is from 4.5 to 8.0. The final product is a dispersion, which may require high energy mixing to break any agglomeration to achieve uniformity. Other formulation ingredients are then added with mixing. The resulting product has a viscosity ranging from 1 to 20,000 cps.

The ophthalmic formulations of the present invention are preferably administered topically to the eye or ear. Typically, topical administration is necessary once or twice per day. The precise dosage regimen is left to the routine discretion of the clinician.

The following examples are intended to illustrate, but not limit, the present invention.

EXAMPLE 1

The formulations shown below in Table 1 were prepared.

TABLE 1

|  | A | B | C | D | E | F |
| --- | --- | --- | --- | --- | --- | --- |
| Betaxolol HCl | 0.28 | 0.28 | 0.28 | 0.28 | 0.28 | 0.28 |
| Dipivefrin HCl | 0.11 | 0.11 | 0.11 | 0.11 | 0.11 | 0.11 |
| Amberlite IRP 69 | 0.35 | 0.35 | 0.45 | 0.45 | 0.45 | 0.45 |
| HEC* | 0.5 | — | — | — | — | — |
| HPMC** | — | 0.5 | 0.4 | 0.4 | — | — |
| Carbopol 934P | — | — | 0.15 | — | 0.15 | 0.4 |
| Xanthan gum | — | — | — | — | — | 0.15 |
| CMC*** | — | — | — | 0.15 | 0.4 | — |
| Mannitol | 2.7 | 2.7 | 2.6 | 2.6 | 2.6 | 2.6 |

TABLE 1-continued

|  | A | B | C | D | E | F |
|---|---|---|---|---|---|---|
| Edetate Disodium | 0.01 | 0.01 | 0.01 | 0.01 | 0.01 | 0.01 |
| Boric Acid | 0.4 | 0.4 | 0.4 | 0.4 | 0.4 | 0.4 |
| Sodium Thiosulfate | 0.2 | 0.2 | 0.2 | 0.2 | 0.2 | 0.2 |
| N-Lauroyl Sarcosinate | 0.03 | 0.03 | 0.03 | 0.03 | 0.03 | 0.03 |
| Benzalkonium Chloride | 0.011 | 0.011 | 0.011 | 0.011 | 0.011 | 0.011 |
| NaOH/HCl | q.s. to pH 5 | q.s. to pH 5 | q.s. to pH 5.5 | q.s. to pH 5.5 | q.s. to pH 5.5 | q.s. to pH 5.5 |
| Purified Water | q.s. to 100 | q.s. to 100 | q.s. to 100 | q.s. to 100 | q.s. to 100 | q.s. to 100 |

*Hydroxyethyl cellulose (Natrosol 250 HR)
**Hydroxypropyl methyl cellulose (K 100 M)
***Sodium carboxymethyl cellulose (Aqualon 7HF)

EXAMPLE 2

The settling and resuspendability rates of Formulation A and modified versions of Formulation A were evaluated as follows. Approximately 5 gm of each formulation were placed in separate measuring cylinders and left standing to monitor (visually) the rate of settling. The height of the sediment (Vs) relative to the total height (Vt) of the formulation was recorded at days 0, 5 and 29. The greater the sediment height, the better the formulation's physical stability. A smaller sediment height indicates a more severe phase separation or "caking." At day 6, each formulation was manually hand-shaken (gentle wrist shaking) to determine the time necessary to resuspend the formulation into a homogenous suspension. The results are shown in Table 2. The modified versions of Formulation A were prepared by adding the indicated amount of carbomer from either a 0.1% or 0.2% stock solution and adding the necessary amount of Formulation A to give a total of about 5 gm. For example, the modified version of Formulation A that contained 0.05% carbomer 934P was prepared by adding 0.25 g of carbomer 934P from 0.1% stock solution and QS to about 5 gm with formulation A.

TABLE 2

|  | Vs/Vt* | | | Time to Resuspend seconds |
|---|---|---|---|---|
|  | Day 0 | Day 5 | Day 29 | Day 6 |
| (a) Formulation A | No settling | 0.2/5.1 | 0.2/5.1 | >30 |
| (b) with 0.05% Carbopol 934P | No settling | — | 0.8/5.1 | — |
| (c) with 0.1% Carbopol 934P | No settling | >4.9/5.1 | 4.0/5.1 | 9 |
| (d) with 0.2% Carbopol 934P | No settling | >4.9/5.1 | 4.8/5.1 | 7 |

*Vs/Vt = volume of sediment or flocculent/total sample volume in the measuring cylinder The settling and resuspendability rates of Formulation B and modified versions of Formulation B were evaluated according to the same procedure described above for Formulation A. The indicated modified versions of Formulation B were prepared in the same way that the modified versions of Formulation A were prepared. The results are shown in Table 3.

TABLE 3

|  | Vs/Vt* | | | Time to Resuspend seconds |
|---|---|---|---|---|
|  | Day 0 | Day 5 | Day 29 | Day 6 |
| (a) Formulation B | No settling | 0.1/2.2 | 0.1/1.7 | 60 |
| (b) with 0.1% Carbopol 934P | No settling | 2.3/2.3 | 1.6/2.3 | 15 |
| (d) with 0.2% Carbopol 934P | No settling | 2.2/2.2 | 2.1/2.2 | 15 |

*Vs/Vt = volume of sediment or flocculent/total sample volume in the measuring cylinder The settling and resuspendability rates of Formulations C–F were evaluated according to the same procedure described above for Formulation A. The results are shown in Table 4.

TABLE 4

| FORMATION | Vs/Vt* Day 20 | Time to resuspend (seconds) Day 4 |
|---|---|---|
| Formulation C (0.4% HPMC + 0.15% Carbopol 934P) | 38/40 | 10 |
| Formulation D (0.4% HPMC + 0.15% CMC) | 2.8/40 | 18 |
| Formulation E (0.4% CMC + 0.15% Carbopol 934P) | 25/40 | 2 |
| Formulation F (0.4% Carbopol 934 P + 0.15% xanthan gum) | 2/40 | 45 |

*Vs/Vt = volume of sediment or flocculent/total sample volume in the measuring cylinder The invention has been described herein with reference to certain preferred embodiments. However, as obvious variations thereon will become apparent to those skilled in the art, the invention is not to be considered as limited thereto.

What is claimed is:

1. In a topically administrable, aqueous suspension composition comprising a basic active component, an ion exchange resin, and a polymeric suspending component, the improvement wherein the polymeric suspending component consists essentially of a combination of a carboxyvinyl polymer and a cellulose polymer selected from the group consisting of hydroxyethyl cellulose; hydroxypropyl cellulose; and carboxymethyl cellulose.

2. The suspension composition of claim 1 wherein the basic active component is selected from the group consisting of beta blockers; pilocarpine; epinephrine; proepinephrine; norepinephrine; pronorepinephrine; clonidine and clonidine derivatives; brimonidine; prostaglandins; steroidal and non-steroidal anti-inflammatory agents; anti-infective agents and anti-allergy agents.

3. The suspension composition of claim 1 wherein the amount of basic active component is about 0.01 to 4.0% (w/v).

4. The suspension composition of claim 1 wherein the ion exchange resin is present in an amount from about 0.05 to about 10% (w/v).

5. The suspension composition of claim 1 wherein the basic active ion exchange resin is present in a 0.5:1–1.5:1 ratio with the basic active.

6. The suspension composition of claim 1 wherein the carboxyl vinyl polymers are characterized as having carboxylic acid functional groups that contain from 2 to 7 carbon atoms per functional group.

7. The suspension composition of claim 1 wherein the amount of carboxyvinyl polymer is from about 0.05 to 1.0%.

8. The suspension composition of claim 1 wherein the amount of cellulose polymer is from about 0.05 to 1%.

9. The suspension composition of claim 1 wherein the composition further comprises one or more components selected from the group consisting of pharmaceutically acceptable buffers; nonionic tonicity-adjusting agents; solubilizing aids; pH-adjusting agents; antioxidants; preservatives; preservative adjuncts; and stabilizing agents.

* * * * *